United States Patent [19]

Kluge et al.

[11] 4,174,399
[45] Nov. 13, 1979

[54] TREATMENT OF LACTIC ACIDOSIS IN RUMINANTS

[75] Inventors: Arthur F. Kluge, Los Altos; Ian T. Harrison, Palo Alto, both of Calif.

[73] Assignee: Syntex (USA) Inc., Palo Alto, Calif.

[21] Appl. No.: 923,276

[22] Filed: Jul. 10, 1978

[51] Int. Cl.$^2$ .................... A61K 31/43; C07D 499/78
[52] U.S. Cl. .................................. 424/271; 424/263; 424/244; 424/270
[58] Field of Search ................... 260/239.1; 424/271, 424/263, 244, 270

[56] References Cited

U.S. PATENT DOCUMENTS

| 3,197,466 | 7/1965 | Chow et al. | 260/239.1 |
| 3,880,846 | 4/1975 | Brever et al. | 260/239.1 |
| 3,997,533 | 12/1976 | Kabbe et al. | 424/246 |

FOREIGN PATENT DOCUMENTS 1392156  4/1975  United Kingdom ................ 260/243 C

OTHER PUBLICATIONS

Perron et al., J. Org. Chem., vol. 20, pp. 3365–3367 (1961).
Naito et al., J. Antibiotics Ser. A, vol. 18, No. 4, pp. 145–153 (1965).

*Primary Examiner*—Gerald A. Schwartz
*Attorney, Agent, or Firm*—Alan M. Krubiner

[57] ABSTRACT

6-(N-vinylureido)penicillanic acids and salts thereof; and processes for preparing such compounds are disclosed. The compounds are useful as inhibitors of lactic acidosis in ruminants.

21 Claims, No Drawings

TREATMENT OF LACTIC ACIDOSIS IN RUMINANTS

BACKGROUND OF INVENTION

1. Field of Invention

This invention relates to penicillin-type compounds having lactic acidosis-inhibitory effects in ruminants and to intermediates and processes for preparing such compounds. In particular, this invention relates to 6-(N'-vinylureido)penicillanic acids and salts thereof; to derivatives and salts thereof; to intermediates for and methods of preparing such compounds. The invention also relates to pharmaceutical compositions containing such compounds and methods for inhibiting lactic acidosis in ruminants.

2. Prior Art

It is common practice in preparing range-fed cattle and other ruminants for market to hold them in "feedlots" for certain periods of time where feed is restricted to "high energy" (carbohydrate) foods that promote rapid weight gain and develop other desirable characteristics in such animals. Consumption of large amounts of high energy feed stuffs required to promote these effects often results in acute indigestion in the ruminants. This disorder is attributable to a series of biochemical and microbiological events that are triggered by an initial rapid accumulation of lactic acid in the rumen. Symptoms of such lactic acidosis initially appear as decreased feed consumption and rate of weight gain (the "off-feed" syndrome) and may ultimately result in death. A considerable volume of information is available concerning the microbiological processes in the rumen that are associated with high energy, feed-caused acute indigestion. Ruminants not accustomed to these high energy diets have fewer numbers of amylolytic, volatile fatty acid (VFA)-producing rumen bacteria than animals that have already adapted to such diet. However, one saccharolytic, amylolytic, lactate-producing rumen organism, *Streptococcus bovus*, is present in approximately equal numbers in both high energy-fed and the range-fed animals. Since the total bacterial numbers are lower in range-fed animals, *S. bovus* is one of the predominant species under this latter feeding regimen. It is recognized that the potential growth rate of *S. bovus* is much more rapid than other rumen bacteria. An abundance of carbohydrate in the rumen of unadapted animals can therefore lead to an almost explosive growth of *S. bovus* with an accompanying increase in lactic acid production and consequent precipitous drop in pH within the rumen. The normal, major species of rumen microorganisms survive poorly, if at all, at this lowered pH. VFA production is therefore inhibited. Further, *S. bovus* fails to grow at the acidity that it ultimately produces. Consequently, lacto bacilli predominate and, if sufficient carbohydrate is available, lactic acid production continues with visible symptoms of lactic acidosis becoming extant. As an attempt to diminish the occurance of lactic acidosis, it has been the practice to increase the energy (carbohydrate) intake of feed-lot cattle gradually in order for the rumen microbial population to become adapted to the change in diet. This adaptation typically is ten days or longer in duration. Consequently, rapid initial weight gains for these ruminants are intentionally sacrificed so as to avoid occurrences of lactic acidosis. In addition, since animals are fed in large groups, sub-clinical occurrences of lactic acidosis still occur throughout the feeding period. It is therefore desirable to permit an alternative, less time-consuming method than the typical adaptation period for preventing accumulation of lactic acid in the rumen following engorgement of high-energy feed stuffs.

SUMMARY

It has now been discovered that the administration of certain penicillanic acids and salts thereof to unadapted, (restricted energy-fed) ruminants on high energy diets prevents the incidence of lactic acidosis in these animals.

In summary, the compounds of the present invention can be represented by the following generic formulas:

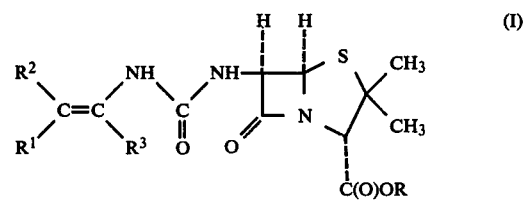

wherein $R^1$, $R^2$ and $R^3$ are individually hydrogen; $C_1$ to $C_{12}$ linear or branched alkyl; $C_6$ to $C_{12}$ carbocyclic aryl optionally substituted with halo, cyano, $C_1$ to $C_6$ linear or branched alkoxycarbonyl, $C_1$ to $C_6$ linear or branched alkyl or $C_1$ to $C_6$ linear or branched alkoxy; or $C_4$ to $C_{11}$ heterocyclic aryl optionally substituted with $C_1$ to $C_6$ linear or branched alkyl or $C_1$ to $C_6$ linear or branched alkoxy, the hetero atom selected from the group nitrogen, oxygen and sulfur; and R is hydrogen or a protecting group selected from t-butyl, diphenylmethyl, benzyl, ortho-nitrobenzyl, para-nitrobenzyl, 3,5-dinitrobenzyl, para-methoxybenzyl, benzhydryl, pivaloxymethyl, phenacyl and $C_2$ to $C_6$ linear or branched haloalkyl; and pharmaceutically acceptable salts thereof with the proviso that at least one of the $R^1$, $R^2$ and $R^3$ is other than hydrogen.

In summary, the pharmaceutical compositions of this invention comprise the compounds of formula (I) and/or pharmaceutically acceptable salts thereof and a pharmaceutically acceptable carrier.

In summary, the method of this invention for reducing of inhibiting lactic alcohols comprises administering an effective amount of the carboxylic acids of formula (I) or a pharmaceutically acceptable salt thereof to mammals suffering from such.

DESCRIPTION OF THE PREFERRED EMBODIMENTS

The compounds useful in the treatment of lactic acidosis in ruminants are represented by the following formula:

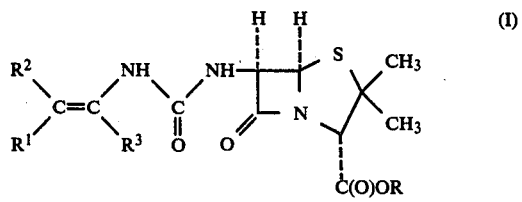

wherein $R^1$, $R^2$ and $R^3$ are individually hydrogen; $C_1$ to $C_{12}$ linear or branched alkyl; $C_6$ to $C_{12}$ carbocyclic aryl optionally substituted with halo, cyano, $C_1$ to $C_6$ linear or branched alkoxycarbonyl, $C_1$ to $C_6$ linear or branched alkyl or $C_1$ to $C_6$ linear or branched alkoxy; or $C_4$ to $C_{11}$ heterocyclic aryl optionally substituted with $C_1$ to $C_6$ linear or branched alkyl or $C_1$ to $C_6$ linear or branched alkoxy, the hetero atom selected from the group nitrogen, oxygen and sulfur; and R is hydrogen or a protecting group selected from t-butyl, diphenylmethyl, benzyl, ortho-nitro-benzyl, para-nitrobenzyl, 3,5-dinitrobenzyl, para-methoxy-benzyl, benzhydryl, pivaloxymethyl, phenacyl and $C_2$ to $C_6$ linear or branched haloalkyl with the proviso that at least one of the $R^1$, $R^2$, and $R^3$ is other than hydrogen.

Also encompassed within the invention are the pharmaceutically acceptable salts of the compounds of formula (I).

It should be noted that the C-6 position ureido-substituent is β-oriented.

With respect to lactic acidosis inhibition, the preferred compounds of formula (I) are those where $R^1$ or $R^2$ or $R^3$ are individually hydrogen; $C_1$ to $C_6$ linear or branched alkyl; $C_6$ to $C_{10}$ carbocyclic aryl optionally substituted with halo, cyano, methoxycarbonyl, ethoxycarbonyl, methyl, ethyl, methoxy or ethoxy; or heterocyclic aryl selected from the group pyrrolyl, thienyl, furyl and pyridyl optionally substituted with methyl, ethyl, methoxy or ethoxy. Most preferably, when $R^2$ and $R^3$ are hydrogen, $R^1$ is alkyl selected from the group methyl, ethyl and isopropyl, particularly methyl; phenyl or naphthyl optionally substituted with fluoro, chloro, bromo, cyano, methoxycarbonyl, ethoxycarbonyl, methyl, ethyl, methoxy or heterocyclic aryl selected from the group pyrolyl, thienyl, furyl and pyridyl. In cases where $R^1$ is hydrogen, preferably $R^2$ and $R^3$ are phenyl or naphthyl optionally substituted with chloro, cyano, methoxycarbonyl or ethoxy-carbonyl, most preferably phenyl or naphthyl; heterocyclic aryl selected from the group, thienyl, furyl and pyridyl optionally substituted with methyl, ethyl, ethoxy or methoxy. In cases where $R^3$ is hydrogen, $R^1$ and $R^2$ are preferably alkyl selected from the group methyl, ethyl and isopropyl, particularly methyl; phenyl or naphthyl optionally substituted with fluoro, chloro, bromo, cyano, methoxycarbonyl or ethoxycarbonyl, most preferably phenyl or naphthyl; heterocyclic aryl selected from the group pyrrolyl, thienyl, furyl and pyridyl optionally substituted with methyl, ethyl, methoxy or ethoxy.

Of the above preferred and most preferred compounds, the particularly preferred compounds are:

6-[$N^3$-(2-phenylvinyl)]ureidopenicillanic acid;
6-[$N^3$-(1,2-diphenylvinyl)]ureidopenicillanic acid;
6-($N^3$-[2-(4-methoxyphenyl)vinyl])ureidopenicillanic acid;
6-($N^3$-[2-(2-methoxyphenyl)vinyl])ureidopenicillanic acid;
6-($N^3$-[2-(4-cyanophenyl)vinyl])ureidopenicillanic acid;
6-($N^3$-[2-(2-naphthyl)vinyl])ureidopenicillanic acid;
6-[$N^3$-(2-ethoxycarbonylvinyl)]ureidopenicillanic acid; and
6-($N^3$-[2-(1-naphthyl)vinyl])ureidopenicillanic acid.

The compounds of the present invention are produced by known methods; they are obtained when isocyanates of the formula $R^1R^2C{=}CR^3NCO$ where $R^1$, $R^2$ and $R^3$ are as previously defined, are reacted with 6-aminopenicillanic esters, more especially the trimethyl silyl ester. The reaction is performed in a known manner in an inert solvent, preferably in methylene chloride, dimethylformamide or acetonitrile, at about 0°–100°, typically at room temperature, for a time sufficient to assure completeness of reaction, typically 30 minutes to 24 hours. See for example, *Journal of Organic Chemistry*, Vol. 36, pp. 3365 (1961), French Pat. No. 1,397,509, and the Examples herein.

The vinylisocyanates, substituted with $R^1$, $R^2$ and $R^3$ are readily prepared by techniques well known to those skilled in the art. The preferred technique herein involves the pyrolysis of a vinyl acylazide (the Curtius Rearrangement), i.e. $R^1R^2C{=}CR^3C(O)N_3$. These azides lose nitrogen gas on heating and intramolecularly rearrange to form the desired isocyanate. Typically, the pyrolysis is carried out by heating the azide from about 30° to about 80° preferably about 35°–45°, in an inert organic solvent such as benzene or toluene for a time sufficient to effect the rearrangement, usually for five minutes to two hours, preferably 20 to 40 minutes. Alternately, the vinyl isocyanates can be prepared by reacting the precursor vinyl carboxylic acids with diphenylphosphoryl azide.

The preparation of the vinyl acylazides may be accomplished by utilizing a variety of reagents in reaction with a vinyl carboxylic acid, i.e. $R^1R^2C{=}CR^3COOH$. Illustrative conversion techniques include the reaction of the carboxylic acid or a salt thereof with thionyl chloride, or ethylchloroformate followed by treatment of the resulting acid chloride or ethyl carbonic anhydride with an alkali metal azide. These reactions have been studied in detail and are described with particularity for example in Chem. Revs., 43, 203 (1948).

It is generally preferred that the respective products of each process step, described hereinabove, and hereinbelow, be separated and/or isolated prior to use as starting materials for subsequent steps. Preparation and isolation can be effected by any suitable means such as for example evaporation, crystallization, column chromatography, thin-layer chromatography, distillation and so forth. Specific illustrations of typical separation and isolation procedures can be had by reference to appropriate examples. However, other equivalent separation procedures could of course also be used. It should also be appreciated that where typical reaction conditions, e.g. temperatures, mole ratios, reaction times and the like, have been given that conditions both above and below these ranges can also be used, though generally less conveniently.

The pharmaceutically acceptable salts of the invention can be prepared according to procedures which are well known in the art, for example, by simply treating the free acid of formula (I) with an inorganic or organic base having the desired salt cation, e.g., sodium hydroxide, potassium hydroxide, triethylamine, ethanolamine, tris(hydroxymethyl)aminomethane and the like. The sodium salts can also be conveniently prepared by treating a solution of the formula (I) carboxylic acid in ethylacetate with an excess of sodium 2-ethylhexanoate.

The acids and salts of the invention have lactic acidosis inhibitory effects in ruminants. They are surprisingly inactive against certain important Gram positive pathogenic bacteria but have superior activity against certain other gram positive organisms. While not wishing to be bound by the following, it is believed that introduction of the compounds of the present invention into the rumen of animals suffering from high-energy, feed-caused lactic acidosis cause the inhibition of growth of the bacterium *S. bovus,* the other rumen bacteria being relatively unaffected by these compounds and follow their normal functions in the ruminant digestive process. Hence, the compounds of formula (I) are specific in the rumen to this bacteria which, in turn, is the bacteria primarily responsible for the undesirable lactic acidosis phenomenon. The compounds can be used to combat or prophylactically prevent problems of this nature in mammals and can be administered in the same manner as penicillin derivative drugs are administered (typically parenterally or orally). The compounds can be administered in a wide variety of dosage forms, either alone or in combination with other pharmaceutically compatible medicaments in the form of pharmaceutical compositions suited for oral or parenteral administration. The dosage forms typically comprise the compounds (typically as pharmaceutically acceptable salts) and a pharmaceutical carrier and are preferably formulated in unit dosage forms to facilitate the simple administration of precise dosages. The pharmaceutical carrier can be either a solid material or liquid in which the compound is dissolved, dispersed or suspended. The dosage form can optionally contain other compatible medicaments, preservatives, emulsifying agents, wetting agents and/or pH buffering agents. Suitable preservatives which can be used include, for example, benzyl alcohol and the like. Suitable buffering agents include for example sodium acetate and pharmaceutical phosphate salts and the like. Liquid dosage forms include, for example, solutions, suspensions, emulsions, syrups, elixirs and so forth. Liquid carriers include for example, water, saline solutions and so forth. Solid dosage forms include, for example, tablets, powders, capsules, pills, and the like. Suitable solid carriers include, for example, pharmaceutical grades of starch, lactose, sodium saccharine, and the like.

The preferred manner of administration of the compounds of the present invention is oral using a convenient daily dosage regimen which can be adjusted according to the degree of lactic acidosis in the ruminants being treated. Generally the compounds of this invention are administered in dosages of about from 0.1 to 10 mg. per kg. per day of body weight. However, the precise effective dosage will vary depending upon the mode of administration, the condition being treated and the host.

The following terms, as used hereinabove and below have the following meaning unless expressly stated to the contrary. The term "$C_1$ to $C_{12}$ linear or branched alkyl" refers to alkyl groups having from 1 through 12 carbon atoms and includes both straight chain and branched chain alkyls such as for example methyl, ethyl, isopropyl, t-butyl, pentyl, n-hexyl, isohexyl, dodecyl and the like. The term "$C_1$ to $C_{12}$ linear or branched alkoxy" refers to alkoxy groups having from 1 through 12 carbon atoms including for example methoxy, ethoxy, isopropoxy, t-butyl, n-butoxy, n-hexoxy and the like. The term "halo" or "halide" refers to the group of fluoro, chloro, bromo and iodo and the corresponding halides. The term "pharmaceutically acceptable salts" refers to those salts of the present invention which do not significantly effect the pharmaceutical properties, e.g., toxicity, effectiveness, etc. of the parent compound such as for example are conventionally used in the pharmaceutical art. The salts of the present invention are pharmaceutically acceptable cation salts with respect to the acid moiety of the compounds of formula (I). Suitable pharmaceutically acceptable cations include, for example the alkali metals, e.g., sodium, potassium, etc.; alkali earth metals, e.g., calcium, etc.; ammonium; organic salts of triethylamine, diethylamine, tris(hydroxymethyl)aminomethane, ethanolamine, chlorine, caffeine, and the like.

The term "$C_5$ to $C_{11}$ heterocyclic aryl" refers to the heterocyclic aromatic compounds having from 5 to 11 carbon atoms and one heteroatom in the ring and having optionally substituted thereon $C_1$ to $C_6$ linear or branched alkyl or $C_1$ to $C_6$ linear or branched alkoxy, e.g. the groups pyridyl such as pyrid-2-yl, pyrid-3-yl, pyrid-4-yl, 1-methyl pyrid-2-yl, etc. The term "$C_6$ to $C_{12}$ carbocyclic aryl" includes those aromatic radicals optionally substituted with $C_1$ to $C_6$ linear or branched alkyl, $C_1$ to $C_6$ linear or branched alkoxy, cyano or $C_1$ to $C_6$ linear or branched alkoxycarbonyl, for example, monocyclic or bicyclic aromatic hydrocarbon radicals especially phenyl or naphthyl which can be optionally mono-substituted or poly-substituted with the previously mentioned substituents. The term "$C_1$ to $C_6$ alkoxycarbonyl" includes the groups methoxycarbonyl, ethoxycarbonyl, n-propoxycarbonyl, t-butoxycarbonyl, t-pentoxycarbonyl and the like. "Vinyl," used herein refers to the group $>C=C<$.

The term "room temperature" refers to about 20° Centigrade and all temperatures and temperature ranges herein refer to degrees Centigrade. All percents refer to weight percents and the term "equivalent mole amount" refers to an amount stoichiometrically equivalent to the other reactant in the reaction referred to.

A further understanding of the invention can be had from the following non-limiting preparations and examples.

EXAMPLE 1

A mixture of 1.8 g. 3-(2-naphthyl))acryloylazide and 15 ml. toluene is heated at reflux for 1 hour. In a separate flask, a mixture of 1.08 g. 6-aminopenicillanic acid, 0.84 g. bis-(trimethylsilyl)acetamide and 10 ml. acetonitrile is stirred at room temperature for 3 hours. The toluene solution and the acetonitrile solution are mixed and the resulting mixture is stirred at room temperature for 18 hours. The mixture is cooled to 0° and 0.4 ml. water is added. The mixture is stirred at room temperature for 30 minutes. Magnesium sulfate (3g.) is added and the mixture is stirred for 30 minutes. The mixture is filtered and, to the filtrate is added a solution of 0.8 g. sodium 2-ethylhexanoate in 77 ml. of a 10:1 mixture of diethyl ether:tetrahydrofuran. The product is collected by filtration and is washed with diethyl ether and acetone to give 1.2g. sodium $6N^3$-[2-(2-naphthyl)]vinyl-)ureidopenicillanate; i.r., (KBr) 1765 cm$^{-1}$; n.m.r. (DMSO) 6.16d (J=15Hz), 1H (vinyl proton), 7.2–8.1 m, 8H (naphthyl and vinyl protons).

In a like manner, using 3-(2-methoxyphenyl)acryloylazide 3-carboethoxyacryloylazide and 3-(4-cyanophenyl)acryloylazide is prepared:

sodium 6-($N^3$-[2-(2-methoxyphenyl)]vinyl-)ureidopenicillanate; i.r. (KBr) 1765 cm$^{-1}$; n.m.r. (DMSO) 3.8 s, 3H (CH$_3$O), 6.15d (J=14Hz), 1H (vinyl proton), 6.7–7.8 m, 5H (phenyl and vinyl protons);

sodium 6-($N^3$-[2-(4-cyanophenyl)[vinyl-)ureidopenicillanate; n.m.r. (DMSO) 6.0 d (J=15Hz), 1H (vinyl proton); 7.3–8.1 m, 5H (phenyl and vinyl protons); and sodium 6-[$N^3$-(2-carboethoxyvinyl)]ureidopenicillanate; i.r. (KBr) 1770, 1700 cm$^{-1}$; n.m.r. (DMSO) 1.17 (J=7Hz), 3H(CH$_3$CH$_2$), 4.08 q (J=7Hz), 2H(CH$_3$CH$_2$); 6.7d (J=15Hz), 1H (vinyl proton), 7.83 d (J=15Hz), 1H (vinyl proton).

EXAMPLE 2

The following Example illustrates a further method for the preparation of the 6-(vinylureido)penicillanic acids of the present invention.

A stirred suspension of 1.08 grams of silylated 6-aminopenicillanic acid in toluene (10 ml.) and 3-phenylacryloylazide is allowed to stir overnight at reflux temperatures. Water (0.4 ml.) is added and the reaction mass stirred for an additional 30 minutes. Sodium 2-hexanoate (0.85 grams) in 8 milliliters of tetrahydrofuran and 75 milliliters of diethyl ether is added to the solution, the mixture centrifuged, washed with 10% tetrahydrofuran/diethylether two times, filtered, and the residue taken up in ethanol. The solid material is reprecipitated with the addition of diethylether and filtered. Sodium 6-[3-(2-phenyl)vinyl]ureidopenicillanate is isolated in 1.76 grams yield; i.r. (KBr) 1765 cm$^{-1}$; n.m.r. (DMSO) 5.9 d (J=15Hz), 1H (vinyl proton), 6.9–7.5 m, 6H (phenyl and vinyl protons).

In a like manner 6-aminopenicillanic acid and the following compounds:

2,3-diphenylacryloylazide;
3-(4-methoxyphenyl)acryloylazide;
3-(2-methoxyphenyl)acryloylazide;
3-(4-cyanophenyl)acryloylazide;
3-(2-naphthyl))acryloylazide;
3-(1-naphthyl)acryloylazide;
3-ethoxycarbonylacryloylazide;

afford the following compounds:

6-([N$^3$-(1,2-diphenylvinyl)])ureidopenicillanic acid;
6-(N$^3$-[1-(4-methoxyphenyl)vinyl])ureidopenicillanic acid;
6-(N$^3$-[1-(2-methoxyphenyl)vinyl])ureidopenicillanic acid;
6-(N$^3$-[2-(4-cyanophenyl)vinyl])ureidopenicillanic acid;
6-(N$^3$-[2-(2-naphthyl)vinyl])ureidopenicillanic acid;
6-(N$^3$-[2-(1-naphthyl)vinyl])ureidopenicillanic acid; and
6-[N$^3$-(2-ethoxycarbonylvinyl)]ureidopenicillanic acid Many modifications and variations of the invention as described hereinabove and below and in the claims can be made without departing from the essence and scope thereof.

What is claimed is:

1. A compound selected from the group of the formula

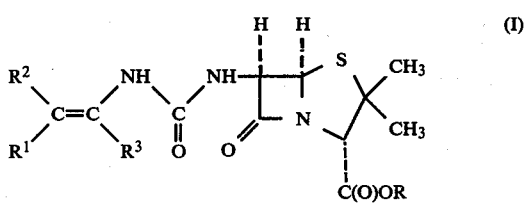

herein R$^1$, R$^2$ and R$^3$ are individually hydrogen; C$_1$ to C$_{12}$ linear or branched alkyl; C$_6$ to C$_{12}$ carbocyclic aryl optionally substituted with halo, cyano, C$_1$ to C$_6$ linear or branched alkoxycarbonyl, C$_1$ to C$_6$ linear or branched alkyl, C$_1$ to C$_6$ linear or branched alkoxy; or C$_4$ to C$_{11}$ heterocyclic aryl optionally substituted with C$_1$ to C$_6$ linear or branched alkyl or C$_1$ to C$_6$ linear or branched alkoxy, the heteroatom selected from the group nitrogen, oxygen and sulfur; and R is hydrogen or a protecting group selected from t-butyl, diphenylmethyl, benzyl, o-nitrobenzyl, p-nitrobenzyl, 3,5-dinitrobenzyl, p-methoxybenzyl, p-methoxybenzyl, benzhydryl, pivaloxymethyl, phenacyl and C$_2$ to C$_6$ linear or branched haloalkyl; and pharmaceutically acceptable salts thereof with the proviso that at least one of R$^1$, R$^2$ and R$^3$ is other than hydrogen.

2. The compound of claim 1 wherein R is hydrogen and the pharmaceutically acceptable salts thereof.

3. The compound of claim 2 wherein R$^1$, R$^2$ and R$^3$ are individually hydrogen; C$_1$ to C$_6$ linear or branched alkyl; C$_6$ to C$_{10}$ carbocyclic aryl optionally substituted with fluoro, chloro, bromo, cyano, methoxycarbonyl, ethoxycarbonyl, methyl, ethyl, methoxy or ethoxy; or heterocyclic aryl selected from the group pyrrolyl, thienyl, furyl, and pyridyl optionally substituted with methyl, ethyl, methoxy or ethoxy.

4. The compound of claim 3 wherein R$^2$ and R$^3$ are hydrogen.

5. The compound of claim 4 wherein R$^1$ is alkyl selected from the group methyl, ethyl and isopropyl.

6. The compound of claim 5 wherein R$^1$ is methyl.

7. The compound of claim 4 wherein R$^1$ is phenyl or naphthyl optionally substituted with chloro, cyano, methoxycarbonyl, ethoxycarbonyl, methyl, ethyl, methoxy or ethoxy.

8. The compound of claim 4 wherein R$^1$ is heterocyclic aryl selected from the group pyrrolyl, thienyl, furyl and pyridyl.

9. The compound of claim 3 where R$^2$ and R$^3$ are other than hydrogen.

10. The compound of claim 9 wherein R$^2$ and R$^3$ are individually alkyl selected from the group methyl, ethyl and isopropyl.

11. The compound of claim 10 wherein R$^2$ and R$^3$ are individually methyl.

12. The compound of claim 9 wherein R$^2$ and R$^3$ are individually phenyl or naphthyl optionally substituted with chloro, cyano, methoxycarbonyl or ethoxycarbonyl.

13. The compound of claim 12 wherein R$^2$ and R$^3$ are individually phenyl or naphthyl.

14. The compound of claim 9 wherein R$^2$ and R$^3$ are individually heterocyclic aryl selected from the group pyrrolyl, thienyl, furyl and pyridyl optionally substituted with methyl, ethyl, methoxy or ethoxy.

15. The compound of claim 3 wherein R$^1$ and R$^2$ are other than hydrogen.

16. The compound of claim 15 wherein R$^2$ and R$^3$ are individually alkyl selected from the group methyl, ethyl and isopropyl.

17. The compound of claim 16 wherein R$^2$ and R$^3$ are individually methyl.

18. The compound of claim 15 wherein R$^2$ and R$^3$ are individually phenyl or naphthyl optionally substituted with chloro, cyano, methoxycarbonyl or ethoxycarbonyl.

19. The compound of claim 18 wherein R$^2$ and R$^3$ are individually phenyl or naphthyl.

20. The compound of claim 15 wherein R$^2$ and R$^3$ are individually heterocyclic aryl selected from the group pyrrolyl, thienyl, furyl and pyridyl optionally substituted with methyl, ethyl, methoxy or ethoxy.

21. A composition for treating lactic acidosis in ruminants comprising administering to said ruminant an effective amount of a compound selected from the group of the formula

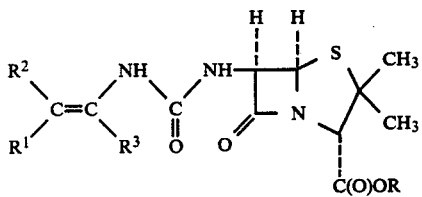

wherein $R^1$, $R^2$ and $R^3$ are individually hydrogen; $C_1$ to $C_{12}$ linear or branched alkyl; $C_6$ to $C_{12}$ carbocyclic aryl optionally substituted with halo, cyano, $C_1$ to $C_6$ linear or branched alkoxycarbonyl, $C_1$ to $C_6$ linear or branched alkyl or $C_1$ to $C_6$ linear or branched alkoxy; or $C_4$ to $C_{11}$ heterocyclic aryl optionally substituted with $C_1$ to $C_6$ linear or branched alkyl or $C_1$ to $C_6$ linear or branched alkoxy, the heteroatom selected from the group nitrogen, oxygen and sulfur; and R is hydrogen or a protecting group selected from t-butyl, diphenylmethyl, benzyl, o-nitrobenzyl, p-nitrobenzyl, 3,5-dinitrobenzyl, p-methoxybenzyl, benzhydryl, pivaloxymethyl, phenacyl and $C_2$ to $C_6$ linear or branched haloalkyl; and pharmaceutically acceptable salts thereof with the proviso that at least one of $R^1$, $R^2$ and $R^3$ is other than hydrogen in admixture with a compatible carrier.

* * * * *